United States Patent [19]
Vigil et al.

[11] Patent Number: 5,320,634
[45] Date of Patent: Jun. 14, 1994

[54] BALLOON CATHETER WITH SEATED CUTTING EDGES

[75] Inventors: Dennis M. Vigil, San Diego; Peter Barath, Los Angeles, both of Calif.

[73] Assignee: Interventional Technologies, Inc., San Diego, Calif.

[21] Appl. No.: 870,148

[22] Filed: Apr. 17, 1992

Related U.S. Application Data

[63] Continuation-in-part of Ser. No. 547,957, Jul. 3, 1990, Pat. No. 5,196,024.

[51] Int. Cl.⁵ .................. A61B 17/32; A61M 25/10
[52] U.S. Cl. ............................. 606/159; 606/170; 606/191; 606/192; 606/194; 604/96
[58] Field of Search .................. 604/96, 98; 606/159, 606/167, 170, 191, 192, 194

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 1,141,364 | 2/1979 | Schultze | 128/349 |
| 3,635,223 | 1/1972 | Klieman | 606/194 |
| 4,140,126 | 2/1979 | Choudhury | 128/325 |
| 4,273,128 | 6/1981 | Lary | 128/305 |
| 4,292,974 | 10/1981 | Fogarty et al. | 128/344 |
| 4,406,656 | 9/1983 | Hattler et al. | 604/280 |
| 4,465,072 | 8/1984 | Taheri | 606/159 |
| 4,490,421 | 12/1984 | Levy | 428/35 |
| 4,608,984 | 9/1986 | Fogarty | 128/344 |
| 4,627,436 | 12/1986 | Leckrone | 128/303.1 |
| 4,685,458 | 8/1987 | Leckrone | 128/303.1 |
| 4,686,982 | 8/1987 | Nash | 128/305 |
| 4,705,517 | 11/1987 | DiPisa, Jr. | 623/12 |
| 4,723,549 | 2/1988 | Wholey et al. | 128/344 |
| 4,787,388 | 11/1988 | Hofmann | 128/344 |
| 4,886,061 | 12/1989 | Fischell et al. | 606/159 |
| 4,966,604 | 10/1990 | Reiss | 606/170 |
| 5,009,659 | 4/1991 | Hamlin et al. | 606/159 |
| 5,042,985 | 8/1991 | Elliott et al. | 606/192 |
| 5,078,725 | 1/1992 | Enderle et al. | 606/193 |
| 5,116,318 | 5/1992 | Hillstead | 606/191 |
| 5,156,610 | 10/1992 | Reger | 606/170 |
| 5,196,024 | 3/1993 | Barath | 606/159 |
| 5,209,749 | 5/1993 | Buelna | 606/159 |

FOREIGN PATENT DOCUMENTS

| | | | |
|---|---|---|---|
| PCT/US90/-00337 | 7/1990 | European Pat. Off. | A61B 17/32 |
| 0414350A1 | 2/1991 | European Pat. Off. | A61M 25/10 |
| 3402573A1 | 8/1985 | Fed. Rep. of Germany | A61M 25/00 |
| 3519626 | 12/1986 | Fed. Rep. of Germany | 606/159 |

(List continued on next page.)

OTHER PUBLICATIONS

B. G. Lary, M.D., *Experimental Maintenance of Life by Intravenous Oxygen, Preliminary Report*, Clinical Congress of the American College of Surgeons, San Francisco, Nov. 5–9, 1951.

(List continued on next page.)

Primary Examiner—K. M. Pfaffle
Attorney, Agent, or Firm—Nydegger & Associates

[57] ABSTRACT

A stenotic dilitation device includes a plurality of elongated atherotomes with cutters embedded in a substrate mounted on the outer surface of a flexible balloon along predetermined crease lines. The atherotomes are aligned along the longitudinal axis of the catheter. The ends of the balloon are attached to a hollow catheter tube over fluid ports in the catheter which establish fluid communication between the catheter and the internal chamber of the balloon. Fluid flow into and out of the chamber will inflate and deflate the balloon. When the balloon is deflated, retraction of the atherotomes toward the longitudinal axis of the catheter causes the creases and lines to form flaps of the balloon membrane material between adjacent atherotomes. In such deflated configuration, the flaps, rather than the cutters of the atherotomes, contact the vessel wall as the device is manipulated into position adjacent a stenotic site. On inflation of the balloon at the stenotic site, the atherotomes are urged against the stenosis to incise the stenosis. The incisions relieve pressure in the wall of the vessel and thus enhance dilation of the vessel by the balloon. After dilation, the balloon is deflated and the device is removed.

15 Claims, 3 Drawing Sheets

FOREIGN PATENT DOCUMENTS

| | | | |
|---|---|---|---|
| WO90/07909 | 7/1990 | PCT Int'l Appl. | A61B 17/32 |
| 1516120 | 10/1989 | U.S.S.R. | 606/191 |
| 1547328 | 6/1979 | United Kingdom | 604/96 |

OTHER PUBLICATIONS

Banning G. Lary, M.D., *Effect of Endocardial Incisions on Myocardial Blood Flow*, Archives of Surgery, Sep. 1963, vol. 87, pp. 424-427 (reprint).

Banning G. Lary, M.D., *Method for Increasing the Diameter of Long Segments of the Coronary Artery*, The American Surgeon, Jan., 1966, vol. 32, No. 1, pp. 33-35 (reprint).

Banning G. Lary, M.D., John G. Chesney, M.D.; Thomas O. Gentsch, M.D., F.C.C.P. and Parry B. Larsen, M. D.; *The "Coronary Myocardial Artery" for Coronary Artery Disease*, Diseases of the Chest, vol. 49, No. 4, Apr., 1966, pp. 412-419 (reprint).

Banning, G. Lary, M.D., *Onlay Vein Graft for the Correction of Coronary Artery Obstruction*, Surgery, vol. 59, No. 4, pp. 547-551, Apr., 1966 (reprint).

Banning G. Lary, M.D. and Roger W. Sherman, M.D., *A Method for Creating a Coronary-Myocardial Artery*, Surgery, vol. 59, No. 6, pp. 1061-1064, Jun., 1966.

Banning G. Lary, *A Method to Create and Correct Stenosis of a Coronary Artery*, Archives of Surgery, vol. 93, pp. 828-830, Nov. 1966.

Banning G. Lary, *An Epicardial Purse String Suture for Closing Coronary Arteriotomy*, The American Surgeon, No. 3, pp. 213-214, Mar., 1967.

Banning G. Lary, M. D., *Surgery for Coronary Artery Disease*, Nursing Clinics of North America, vol. 2, No. 3, pp. 537-542, Sep., 1967.

Banning G. Lary, M.D.; Antonio Camelo, M. D.; Roger W. Sherman, M.D.; and Thomas J. Noto, M.D., *Myocardial Revascularization Experiments Using the Epicardium*, Archives of Surgery, vol. 98, pp. 69-72, Jan., 1969.

Banning G. Lary, M.D., *Coronary Artery Resection and Replacement by a Blood Conduit*, Surgery, vol. 65, No. 4, pp. 584-589, Apr., 1969.

Banning G. Lary, M.D.; Roger W. Sherman, M.D.; Sonya S. Glasser; Joan McDermott; and Frank Gollan, M.D., *Experimental Vein Angioplasty of the Circumflex Coronary Artery*, Journal of Surgical Research, vol. 17, pp. 210-214, 1974.

Banning G. Lary, M.D., *Coronary Artery Incision and Dilation*, Archives of Surgery, vol. 115, pp. 1478-1480, Dec., 1980.

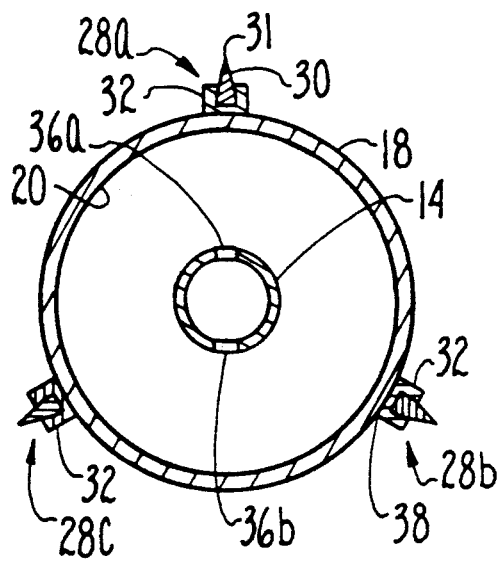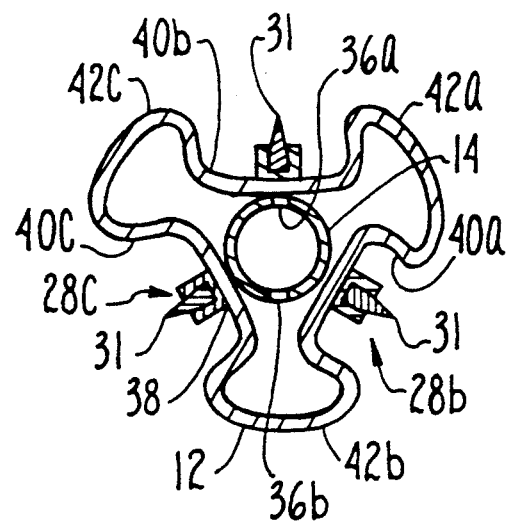
Fig. 3A  Fig. 3B
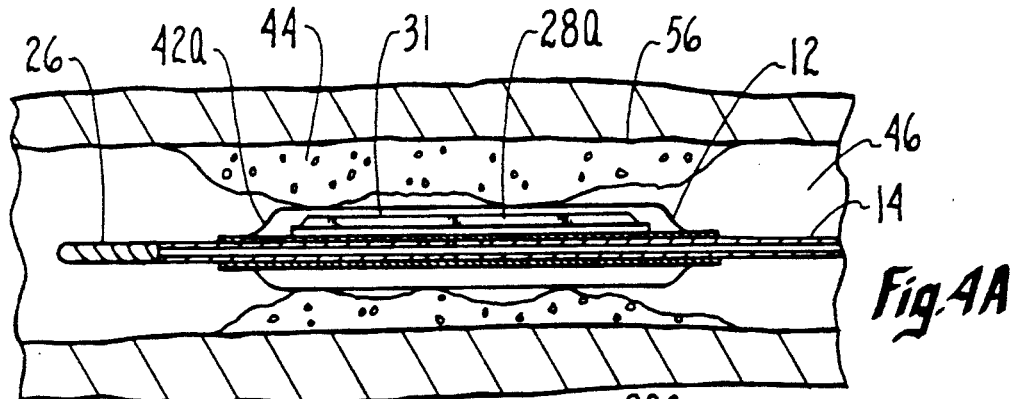
Fig. 4A
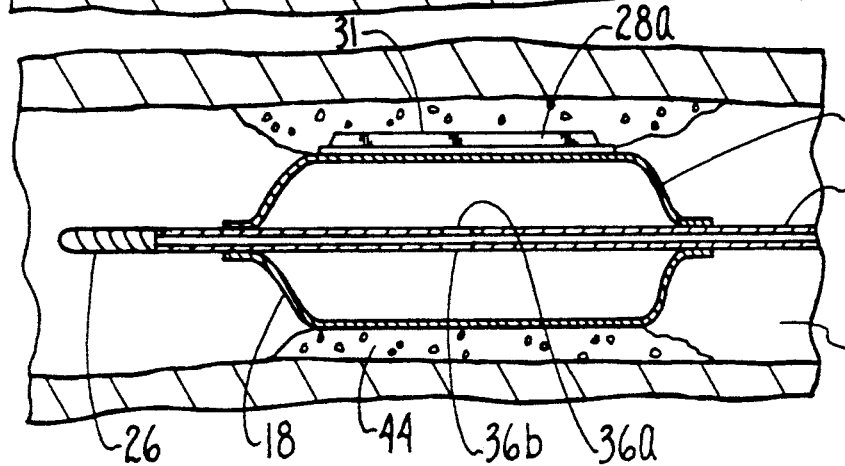
Fig. 4B

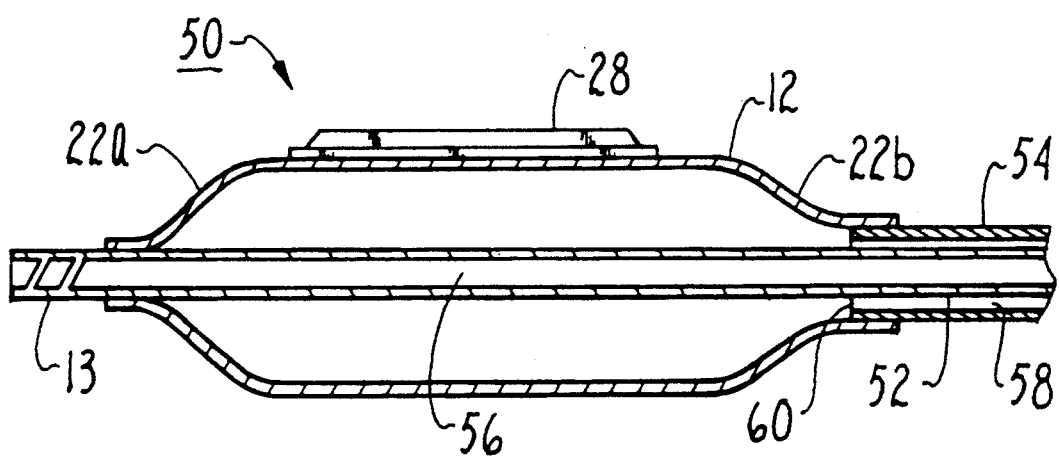

BALLOON CATHETER WITH SEATED CUTTING EDGES

This is a continuation-in-part of U.S. patent application Ser. No. 07/547,957, now U.S. Pat. No. 5,196,024, filed on Jul. 3, 1990.

FIELD OF THE INVENTION

The present invention relates generally to devices which treat stenoses in blood vessels. More particularly, the present invention relates to angioplasty devices. The present invention particularly, though not exclusively, relates to an angioplasty device which enhances dilatation of a vessel wall across a stenotic section by incising the stenosis to relieve stress in the vessel during dilatation.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of blockages, termed stenoses, which reduce blood flow through the arteries. Consequently, several methods have been introduced to alleviate the effects of plaque build-up restricting the artery. One such method is a procedure termed angioplasty, which uses an inflatable device positioned at the stenosis to dilate the artery. A typical angioplasty device is disclosed in U.S. Pat. No. 4,896,669 to Bhate et al. The device of Bhate et al is typical and, like other angioplasty devices, includes an inflatable balloon which is attached to the distal end of a hollow catheter. The proximal end of the catheter is attached to a fluid source. To treat an arterial stenosis, the balloon is introduced into the artery in a deflated state and guided through the artery over a guide wire to a position adjacent the stenosis. Fluid from the fluid source is then infused into the balloon via the catheter to inflate the balloon. As the balloon expands, it presses against the arterial wall in the region of the stenosis, dilating the artery at the stenosis and restoring it to a sufficient size for adequate blood flow. The balloon is then deflated and removed from the artery, thereby completing the treatment.

While effective for dilating blood vessels, angioplasty devices simultaneously traumatize the tissue of the vessel wall. The dilatation procedure can sometimes excessively stress the tissue of the wall, even to the point of tearing it. Dire consequences to the patient such as an acute occlusion or a thrombosis can result. To address this shortcoming, angioplasty devices have been developed which employ a cutting element in cooperation with the balloon to reduce stress on the tissue of the vessel wall.

One particular disadvantage of an angioplasty device which employs a cutting element, however, is that the cutting element can be exposed to surrounding healthy tissue during placement of the device in the blood vessel of a patient, even when the balloon is deflated. As a result, the sharpened cutting element can inadvertently damage healthy tissue with which it comes in contact.

Accordingly, the present invention recognizes a need to provide an angioplasty device which effectively employs a cutting element in cooperation with a balloon during a procedure for dilatation of a stenosis, yet protects healthy tissue from damage during placement of the device in a blood vessel to be treated.

It is therefore an object of the present invention to provide an angioplasty device that can dilate a vessel while minimizing trauma to the tissue of the vessel wall by forming stress-relieving incisions therein. Another object of the present invention is to provide an angioplasty device having a sharp cutting element which can be guided into an artery where the stenosis occurs without significantly damaging healthy tissue along its path. Yet another object of the present invention is to provide an angioplasty device that is relatively easy to use and cost-effective to manufacture.

SUMMARY OF THE INVENTION

A balloon catheter is provided for enhancing dilatation of a vessel wall across a stenotic segment by incising the stenosis to relieve stress in the vessel during dilatation by the balloon. In accordance with the present invention, such a device comprises a balloon, a plurality of atherotomes mounted on the outer surface of the balloon, and a catheter in fluid communication with the balloon. An atherotome, for purposes of the present invention, is taken to be a metallic cutting structure embedded in a polyurethane substrate.

Prior to insertion of the device into the vessel, the balloon is deflated. When deflated, each atherotome mounted on the outer surface of the deflated balloon is aligned along the longitudinal axis of the catheter and is circumferentially equidistant from each adjacent atherotome. Further, each atherotome is attached to the balloon along a crease in the balloon that is longitudinal to the axis of the catheter. As attached, the cutting structure of each atherotome projects radially outward from the axis of the catheter. Retraction of the atherotomes toward the longitudinal axis of the catheter during deflation of the balloon forms a flap in the balloon between adjacent atherotomes. Each flap has a folded edge that is generally parallel to the axes of each atherotome and the catheter. In such a deflated insertion configuration, the folded edges and flaps, rather than the cutting structure of the atherotomes, contact the vessel wall as the device is manipulated into position adjacent a stenotic site, thus shielding the unoccluded vessel walls from contact with the cutting edges of the atherotomes.

Following insertion of the device through the vessel and into contact with stenoses, the balloon is inflated. The atherotomes aligned on the outer surface of the balloon are urged into contact with the plaque creating the stenosis. As the balloon is further inflated, the stenosis is incised by the cutting structure of the atherotomes. The incisions relieve stress in the wall of the vessel and enhance dilation of the vessel. It will be appreciated that the balloon may be guided to the stenotic segment through a protective sheath to further minimize the possibility of damage to the vessel wall. At the stenosis, the balloon can then be extended from the sheath and positioned across the stenosis.

After dilatation of the vessel, the balloon is deflated. Deflation of the balloon causes the balloon to collapse at the creases and have the atherotomes resume their retracted positions along the creases. Again, during withdrawal of the device from the vessel, the flaps and folded edges of the flaps will shield the wall of the vessel from the cutting structure of the atherotomes.

The novel features of this invention, as well as the invention itself, both as to its structure and its operation, will be best understood from the accompanying description, in which similar characters refer to similar parts.

BRIEF DESCRIPTION OF THE DRAWINGS

FIG. 3A is a cross-sectional view of the stenotic dilatation device of the present invention as seen along line 3—3 in FIG. 1.

FIG. 3B is a cross-sectional view of the stenotic dilatation device of the present invention as shown in FIG. 3A, but showing the balloon deflated.

FIG. 4A is a schematic cross-sectional view of the deflated device of the present invention as seen along line 4—4 in FIG. 1 within its intended operational environment.

FIG. 4B is a schematic cross-sectional view of the inflated device of the present invention as seen along line 4—4 in FIG. 1 within its intended operational environment.

FIG. 5 is a section view of an alternate embodiment of the present invention, incorporating a dual lumen catheter.

DESCRIPTION OF PREFERRED EMBODIMENTS

Figure 1:
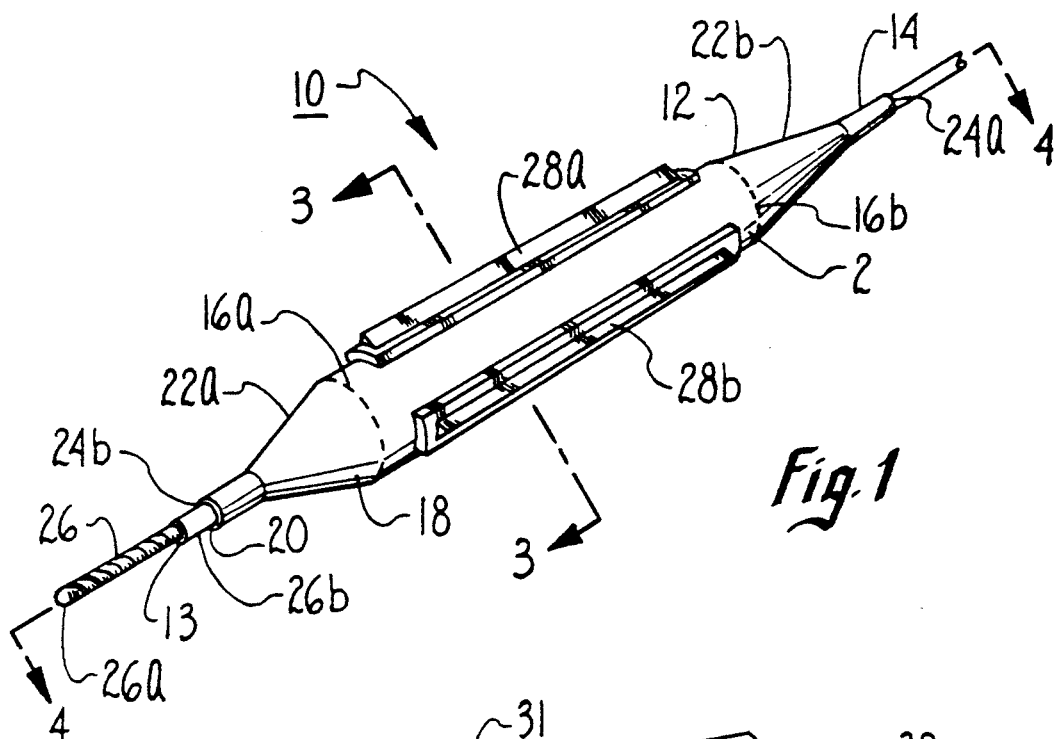
FIG. 1 is a perspective view of the present invention showing the atherotomes mounted on the inflated balloon.

Referring initially to FIG. 1, the stenotic dilatation device of the present invention is shown inflated and generally designated 10. Device 10 includes a balloon 12 positioned near the distal end 13 of a hollow catheter 14. Catheter 14 has an extended length and is connected at its proximal end to a conventional apparatus (not shown) which has a plurality of ports formed therein. The use of various apparatus are well known to those skilled in the art for a variety of functions including placement of a guide wire in a catheter during positioning of a balloon assembly in a blood vessel, pressurized infusion of fluids into a balloon assembly using a catheter, or withdrawal of fluids or other materials from a balloon assembly through a catheter under vacuum during operation of an angioplasty device.

FIG. 1 also shows that inflated balloon 12 is substantially cylindrical between a distal annulus 16a of the outer surface 18 of balloon 12 and a proximal annulus 16b of outer surface 18 of balloon 12. As shown, end 22a of balloon 12 is inwardly tapered from distal annulus 16a toward catheter 14. Similarly end 22b of balloon 12 is inwardly tapered from proximal annulus 16b toward the catheter 14. As further shown in FIG. 1, tapered ends 22a, 22b are formed with an aperture 24a, 24b accessing the interior of balloon 12 and are substantially coaxial with the longitudinal axis of catheter 14.

As further shown in FIG. 1, catheter 14 enters balloon 12 through proximal aperture 24a and exits balloon 12 through distal aperture 24b. Accordingly, catheter 14 coaxially extends through balloon 12 and sealingly engages the inner surface 20 of balloon 12 (as shown in FIG. 3A) at apertures 24a, 24b to prevent fluid communication between the interior of balloon 12 and apertures 24a, 24b. Sealing engagement is provided by adhesive bonding, thermal bonding, or any means well known in the art. FIG. 1 also shows that extending from distal end 13 of catheter 14 is a flexible tip 26 which is made by forming a continuous helical slit along the tip 26 from distal point 26a of tip 26 to proximal point 26b of tip 26.

FIG. 1 further shows balloon 12 includes a plurality of substantially identical atherotomes 28a, 28b, 28c mounted on outer surface 18 of balloon 12 aligned along the longitudinal axis of catheter 14 and circumferentially equidistant from each adjacent atherotome. (Only atherotomes 28a, 28b are visible in the view of FIG. 1.) Further, although only these atherotomes are shown for device 10 in FIG. 1 it will be appreciated that additional atherotomes 28 can be employed.

Figure 2A:
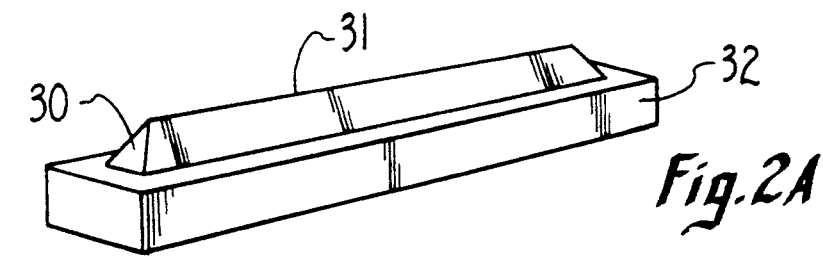
FIGS. 2A, 2B, and 2C are perspective views of the components of an atherotome shown before attachment to the outer surface of the balloon.
Figure 2B:
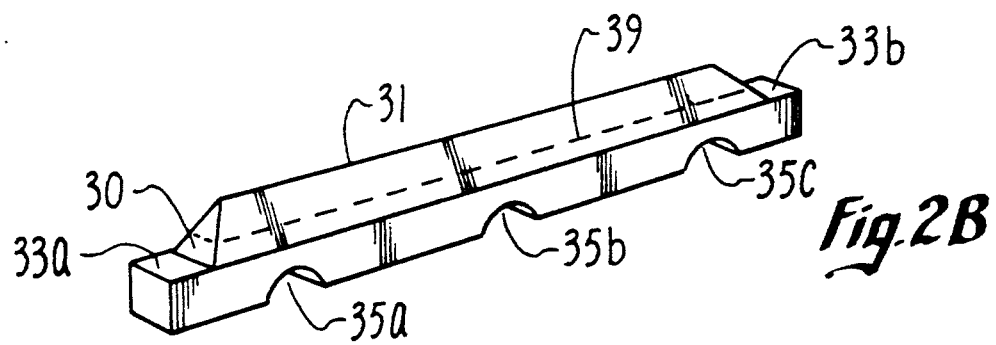
Figure 2C:
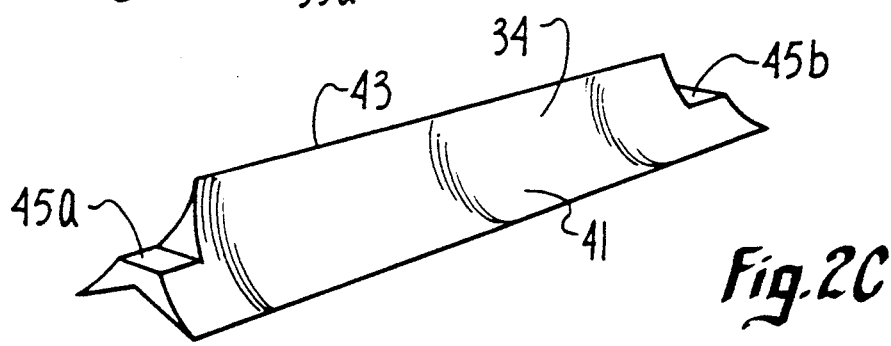

FIGS. 2A, 2B, and 2C are perspective views of components and embodiments of the atherotomes 28. As shown in FIG. 2A, an atherotome 28 for the present invention can be a metallic cutting structure 30 embedded in a substrate 32 of resinous material such as polyurethane. As shown, the cutting structure has a cutting edge 31. FIG. 2B shows the preferred embodiment of cutting structure 30 prior to being embedded into substrate 32. In FIG. 2B it is shown that the structure 30 has a cutting edge 31, step extensions 33a and 33b and, for purposes of the preferred embodiment, a plurality of semi-circular grooves 35a,b, and c forward into the base 37. As shown, the grooves 35a,b,c which are each perpendicular to the longitudinal axis of structure 30 for enhanced flexibility of the structure 30. As indicated in FIG. 2B, structure 30 will be embedded into polyurethane substrate 32 (see FIG. 2A) to cover the structure 30 from hash-marked line 39.

FIG. 2C shows an alternate embodiment of a cutter device 34 which is also embeddable in a polyurethane substrate 32. As shown, the cutter device 34 has a base 41 formed with a cutter edge 43, and integral step extensions 45a and 45b.

As indicated in FIG. 1, the atherotomes 28a, 28b, 28c will be as shown in FIG. 2A. Atherotome 28 may, however, be of an embodiment as shown in FIG. 2B or 2C. Either way they are attached by an adhesive to outer surface 18 of balloon 12 along the longitudinal axis of catheter 14 and circumferentially equidistant from each adjacent atherotome.

The details of the stenotic dilatation device 10 are perhaps best seen with reference to FIGS. 3A and 3B. Referring initially to FIG. 3A, a cross-sectional view of device 10 along line 3—3 in FIG. 1, balloon 12 is shown in an inflated configuration. The thicknesses of balloon 12 between outer surface 18 and inner surface 20 is exaggerated for purposes of illustration. Atherotomes 28a, 28b, 28c are shown attached to balloon 12 and substantially equidistant from each adjacent atherotome. Further, they are aligned along the longitudinal axis of catheter 14. The present embodiment of device 10 shows three atherotomes, but four or more atherotomes may be attached to balloon 12 in accordance with the present teaching.

FIGS. 3A and 3B show catheter 14 extending coaxially through balloon 12. Catheter 14 is shown as a single lumen catheter, although multiple lumen catheters, as are well known in the art, may be employed in device 10. One or more ports 36a, 36b in the wall of catheter 14 are shown positioned within the interior of balloon 12 to enable the infusion or withdrawal of fluid from balloon 12 through catheter 14. Referring to FIG. 3B, a cross-sectional view of device 10 along line 3—3 in FIG. 1, balloon 12 of stenotic dilatation device is shown in a deflated configuration prior to insertion into a blood vessel. Balloon 12 will also assume this configuration after incisions are made in a stenosis and preparatory to removal of device 10 from the vessel. As shown in FIG. 3B, when balloon 12 is deflated, each atherotome 28 mounted on outer surface 18 of balloon 12 is still aligned along the longitudinal axis of catheter 14 and is circumferentially equidistant from each adjacent atherotome 28. As further shown in FIG. 3B, on deflation of balloon 12, outer surface 18 of balloon 12 is reconfigured and a plurality of creases 38a, 38b, 38c are formed on outer surface 18 of balloon 12, which result in a plurality of concave sides 40a, 40b, 40c. In pairs these concave sides 40a,b,c form flaps 42a, 42b, 42c which are actually folds in the surface of the balloon 12 between creases 38a, 38b, 38c respectively. Thus, upon retraction of atherotomes 28a, 28b, 28c, toward the longitudinal axis of catheter 14 during deflation of balloon 12, each pair of the flaps 42a, 42b, 42c, in balloon 12 straddle one of the atherotomes 28a, 28b, 28c. Flaps 42a, 42b, 42c are shown to extend substantially the entire length of balloon 12 between distal annulus 16a and proximal annulus 16b, to shield the lumen of an artery from contact with cutting edges 32 of the atherotomes 28.

Referring now to FIG. 5, an alternate embodiment of the present invention incorporates a dual lumen catheter which is shown and generally designated 50. As shown, dual lumen catheter 50 includes an inner catheter 52 which is coaxially aligned inside an outer catheter 54. Importantly, inner catheter 52 has a central lumen 56 which extends the length of dual lumen catheter 50 for receiving a guide wire therethrough. Further, the outer diameter of inner catheter 52 is sufficiently shorter than the inner diameter of outer catheter 52 to establish a fluid lumen 58 between the coaxial catheters 52 and 54. This fluid lumen 58 terminates at a port 60 which is located inside balloon 12. FIG. 5 also shows that the proximal tapered end 22b of balloon 12 is attached to the outer surface of outer catheter 54, and that the distal tapered end 22a of balloon 12 is attached to the outer surface of inner catheter 52. Consequently, with a fluid tight seal between distal tapered end 22a and catheter 52 there can only be fluid communication with balloon 12 through fluid lumen 58.

OPERATION

In the operation of stenotic dilatation device 10, reference is made to FIGS. 4A and 4B. Initially, balloon 12 is deflated while positioned at the stenosis 44 within artery 46 as shown in FIG. 4A. Positioning of device 10 is performed in accordance with well-known surgical techniques and may employ a guide wire (not shown) threaded through catheter 14 as discussed above in conjunction with FIG. 5.

Once stenotic dilatation device 10 is in place at stenosis 44, it is inflated as shown in FIG. 4B by infusion of fluids from a fluid source (not shown) into balloon 12 through catheter 14 and ports 36a, 36b. Inflation of balloon 12 causes cutting edge 31 in each atherotome 28a, 28b, 28c to incise stenosis 44. This relieves some stress on the wall of artery 46 while dilating stenosis 44. The incisions made in stenosis 44 correspond in length to the length of atherotomes 28a, 28b, 28c and are predetermined to be shallower than the wall of artery 46 so as not to penetrate through artery 46. After balloon 12 incises and dilates stenosis 44, it is deflated by withdrawing fluid from balloon 12 under vacuum through catheter 14 and ports 36a, 36b. Stenotic dilatation device 10 is then removed from artery 46.

While the particular stenotic dilatation device as herein shown and disclosed in detail is capable of obtaining the objects and providing the advantages hereinbefore stated, it is understood that this particular treatment device is merely illustrative of presently preferred embodiments of the invention. It is further understood that the present invention is not intended to be so limited and that other embodiments are further possible within the scope of the present invention.

We claim:

1. An angioplasty device for dilating a stenosis in a blood vessel comprising:
   a catheter having a distal end and a proximal end;
   a flexible and substantially cylindrical balloon membrane having an inner surface, an outer surface, a distal end, and a proximal end, said distal end of said balloon membrane being attached near the distal end of said catheter, and said proximal end of said balloon membrane being attached to said catheter at a distance proximal from the distal end of said catheter; and
   a plurality of atherotomes mounted on the outer surface of said balloon membrane and aligned along the longitudinal axis of said catheter; wherein
   each of said atherotomes comprises a cutting structure with a base, and said base is embedded in a substrate mounted on the outer surface of the balloon membrane.

2. A device as recited in claim 1, wherein said catheter is in fluid communication with said balloon membrane through fluid ports formed in said catheter between said distal end and said proximal end of said balloon membrane.

3. A device as recited in claim 1, wherein said cutting structure and said base is formed from metal.

4. A device as recited in claim 1, wherein:
   each said atherotome is permanently mounted on said outer surface of said balloon membrane with an adhesive material;
   said adhesive material is applied to the outer surface of said balloon membrane; and
   said substrate is attached to said outer surface of said balloon membrane by said adhesive material.

5. A device as recited in claim 1, wherein said substrate is formed from a resinous material.

6. A device as recited in claim 1, wherein said substrate is made of polyurethane.

7. A device as recited in claim 1, wherein said plurality of said atherotomes consists of three or more of said atherotomes.

8. A device as recited in claim 1, wherein said balloon membrane has a plurality of flaps formed thereon between said adjacent atherotomes when said balloon membrane is deflated.

9. A device as recited in claim 1 wherein each said atherotome is circumferentially equidistant from each adjacent said atherotome.

10. An angioplasty device for dilating a stenosis in a blood vessel comprising:
    a catheter having a distal end and a proximal end;
    a flexible and substantially cylindrical balloon membrane having an inner surface, an outer surface, a distal end, and a proximal end, said distal end of said balloon membrane being attached near the distal end of said catheter, and said proximal end of said balloon membrane being attached to said catheter at a distance proximal from the distal end of said catheter; and a plurality of atherotomes mounted on the outer surface of said balloon membrane and aligned along the longitudinal axis of said catheter; wherein each of said atherotomes comprises a cutting structure with a base, and said base is embedded in a substrate; and said structure is formed having step extensions in the base of each said structure for permanently embedding said structure in said substrate.

11. An angioplasty device for dilating a stenosis in a blood vessel comprising:

a catheter having a distal end and a proximal end;

a flexible and substantially cylindrical balloon membrane having an inner surface, an outer surface, a distal end, and a proximal end, said distal end of said balloon membrane being attached near the distal end of said catheter, and said proximal end of said balloon membrane being attached to said catheter at a distance proximal from the distal end of said catheter; and a plurality of atherotomes mounted on the outer surface of said balloon membrane and aligned along the longitudinal axis of said catheter; wherein each of said atherotomes comprises a cutting structure with a base, and said base is embedded in a substrate; and said structure is formed having a plurality of semi-circular grooves formed into the base of said structure to enhance longitudinal flexibility of said structure.

12. An angioplasty device for dilating a stenosis in a blood vessel, comprising:

a balloon membrane having an outer surface and having a substantially cylindrical shape when inflated and forming a plurality of concave sides when deflated;

a plurality of atherotomes, each of said atherotomes having a cutting structure embedded in a substrate with a cutting edge of the structure protruding from said substrate, said substrate being mounted on the outer surface of said balloon membrane to align said atherotome along the longitudinal axis of said balloon membrane and circumferentially position said atherotomes equidistant from each adjacent said atherotome; and a plurality of creases formed in the surface of said balloon membrane to form flaps in said balloon membrane when said balloon membrane is deflated each crease being in substantially parallel alignment with the longitudinal axis of said balloon membrane to provide an attachment point for one said atherotome and position said atherotome between said flaps.

13. An angioplasty device as recited in claim 12, wherein said substrate is made of polyurethane.

14. An angioplasty device for dilating a stenosis in a blood vessel, comprising:

a balloon membrane having an outer surface and having a substantially cylindrical shape when inflated and forming a plurality of concave sides when deflated;

a plurality of atherotomes, each of said atherotomes having a cutting structure embedded in a substrate with a cutting edge of the structure protruding from said substrate, said substrate being mounted on the outer surface of said balloon membrane to align said atherotome along the longitudinal axis of said balloon membrane and circumferentially position said atherotomes equidistant from each adjacent said atherotome; and a plurality of creases formed in the surface of said balloon membrane to form flaps in said balloon membrane when said balloon membrane is deflated each crease being in substantially parallel alignment with the longitudinal axis of said balloon membrane to provide an attachment point for one said atherotome and position said atherotome between said flaps;

wherein said structure is formed having step extensions permanently embedding said structure in said substrate.

15. An angioplasty device as recited in claim 14, wherein said structure is formed having a plurality of semi-circular grooves in said structure.

* * * * *